US007105168B1

(12) United States Patent
Carmeliet et al.

(10) Patent No.: US 7,105,168 B1
(45) Date of Patent: Sep. 12, 2006

(54) METHOD OF IMPROVING ISCHEMIC MUSCLE FUNCTION BY ADMINISTERING PLACENTAL GROWTH FACTOR

(75) Inventors: Peter Carmeliet, Oud-Heverlee (BE); Désiré Collen, London (GB)

(73) Assignee: D. Collen Research Foundation VZW, Leuven (BE)

( * ) Notice: Subject to any disclaimer, the term of this patent is extended or adjusted under 35 U.S.C. 154(b) by 49 days.

(21) Appl. No.: 10/454,242

(22) Filed: Jun. 4, 2003

Related U.S. Application Data

(63) Continuation-in-part of application No. 10/182,359, filed on Sep. 23, 2002, now Pat. No. 6,930,089.

(60) Provisional application No. 60/386,116, filed on Jun. 4, 2002.

(51) Int. Cl.
*A61K 38/18* (2006.01)
*C07K 14/475* (2006.01)

(52) U.S. Cl. .................... 424/198.1; 514/12; 530/350; 530/399

(58) Field of Classification Search .................... None
See application file for complete search history.

(56) References Cited

U.S. PATENT DOCUMENTS 5,919,899 A * 7/1999 Persico et al. .............. 530/350

FOREIGN PATENT DOCUMENTS

| GB | 2 332 373 A | 6/1999 |
| WO | WO 97/14307 A1 | 4/1997 |
| WO | WO 98/00493 A1 | 1/1998 |
| WO | WO 98/07832 A1 | 2/1998 |
| WO | WO 99/40197 A2 | 8/1999 |

OTHER PUBLICATIONS

Maglione et al., Proc Natl Acad Sci USA 1991, vol. 88(20): pp. 9267-9271.*
Michael, K. (2000). Relationship of skeletal muscle atrophy to functional status: A systematic research review. Biological Research Nursing. 2(2):117-131.*
Ngo et al. (1994). Computational complexity, protein structure prediction, and the Levinthal paradox. In Merz and Le Grand (Eds.) The Protein Folding Problem and Tertiary Structure Prediction. Birkhauser:Boston, pp. 492-495.*
Wells, J.A. (1990). Additivity of mutational effects in proteins. Biochemistry 29:8529-8517.*
Pettit et al. (1998). The developmemt of site-specific drug-delivery systems for protein and peptide biopharmaceuticals. Trends Biotechnol 16: 343-349.*
Breier, "Expresion of vascular endothelial growth factor during embryonic angiogenesis and endothelial cell differentiation", Development, vol. 114, 1992, pp. 521-532.
Cao, "In vivo Angiogenic Activity and Hypoxia Induction of Heterodimers of Placenta Growth Factor/Vascular Endothelial Growth Factor", J. Clin. Invest., vol. 98, 1996, pp. 2507-2511.

Carmeliet, "VEGF gene therapy: stimulating angiogenesis or angioma-gensis?", Nature Medicine, vol. 6, No. 10, Oct. 2000, pp. 1102-1103.
Carmeliet, "Synergism between vascular enodthelial growth factor and placental growth factor contributes to angiogenesis and plasma extravasation in pathological conditions", Nature Medicine, vol. 7, No. 5, May 2001, pp. 575-583.
Conn, "Purification of a glycoprotein vascular endothelial cell mitogen from a rat glioma-derived cell line", Prod. Natl Acad.Sa., vol. 87, Feb. 1990, pp. 1323-1327.
Connolly, "Human Vascular Permeability Factor", The Journal of Biological Chemistry, vol. 264, No. 33, Nov. 25, 1989, pp. 20017-20024.
Connolly, "Tumor Vascular Permeability Factor Stimulates Endothelial Cell Growth and Angiogenesis", J. Clin. Invest., vol. 84, Nov. 1989, pp. 1470-1478.
Connolly, "Vascular Permeability Factor: A Unique Regulator of Blood Vessel Function", Journal of Cellular Biochemistry, No. 47, 1991, pp. 219-223.
Couffinhal, "Impaired Collateral Vessel Developmemt Associated With Reduced Expression of Vascular Endothelial Growth Factor in ApoE—Mice", J. Am. Heart Assn, 1999, pp. 3188-3198.
Deindl, "Role of Ischemia and of Hypoxia-Inducible Genes in Arteriogenesis After Femoral Artery Occlusion in the Rabbit", J. Am. Heart Assn., 2001, pp. 779-786.
DiSalvo, "Purification and Characterization of a Naturally Occurring Vascular Endothelial Growth Factor—Placenta Growth Factor Heterodimer", Journal of Biological Chemistry, vol. 270, No. 13, Mar. 31, 1995, pp. 7717-7723.
Ferrara, "The Vascular Endothelial Growth Factor Family of Polypeptides", Journal of Cellular Biochemistry, vol. 27, 1991, pp. 211-218.
Henzel, "Pituitary follicular cells secrete a novel heparin-binding growth factor specific for vascular endothelial cells", Biochem Biophys Res Coomun., vol. 161, No. 2, Jun. 15, 1989, pp. 851-858.
Folkman, "Angiogenesis", Journal of Biological Chemistry, vol. 267, No. 16, Jun 5, 1992, pp. 10931-10934.
Gospodarowicz, "Isolation and characterization of a vascular endothelial cell mitogen produced by pituitary-derived folliculo stellate cells", Proc. Natl. Acad. Sci., vol. 86, Oct. 1989, pp. 7311-7315.
Klagsbrun, "Regulators of Angiogenesis", Annu. Rev. Physiol., vol. 53, 1991, pp. 217-239.
Hariawala, "VEGF Improves Myocardial Blood Flow but Produces EDRF-Mediated Hypotension in Porcine Hearts", Journal of Surgical Research, vol. 63, pp. 77-82.
Henry, "The VIVA Trial", Vascular Endothelial Growth Factor in Ischemia for Vascular Angiogenesis, J. Am. Heart Assn., 2003, pp. 1359-1365.

(Continued)

*Primary Examiner*—Brenda Brumback
*Assistant Examiner*—Jon M Lockard
(74) *Attorney, Agent, or Firm*—Clark & Elbing LLP

(57) ABSTRACT

The present invention relates to prevention and treatment of strokes and ischemic diseases and to post-ischemic therapeutic treatment. The invention furthermore relates to the use of a growth factor for treating, more particularly restoring the function of ischemic tissue, in particular muscles such as myocardium and skeletal muscles.

6 Claims, 2 Drawing Sheets

OTHER PUBLICATIONS

Isner, "Angiogenesis and vasculogenesis as therapeutic strategies for postnatal neovascularization", vol. 103, No. 9, May 1999, pp. 1231-1236.

Levy, "An Endothelial Cell Growth Factor from the Mouse Neuroblastoma Cell Line NB41", Growth Factors, vol. 2, 1989, pp. 9-19.

Maglione, "Isolation of a human placenta cDNA coding for a protein related to the vascular permeability factor", Proc. Natl. Acad. Sci., vol. 88, Oct. 1991, pp. 9267-9271.

Frelin, "VEGF: A Mediation of Hypoxic Angiogenesis," Medicine Sciences 13:886-892 (1997).

* cited by examiner

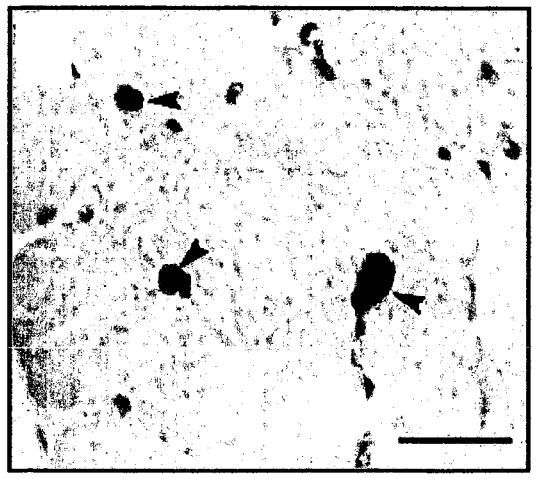
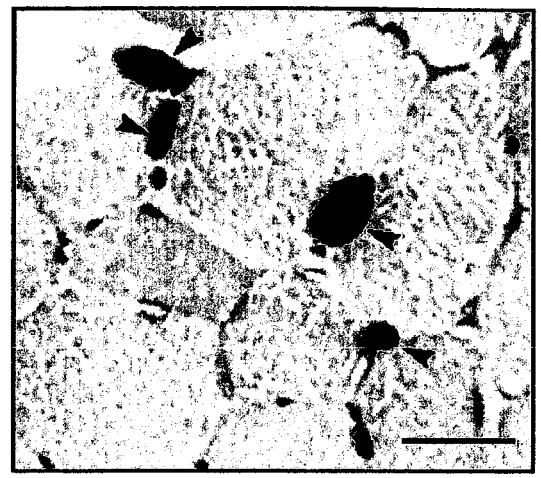
Figure 3
Figure 4
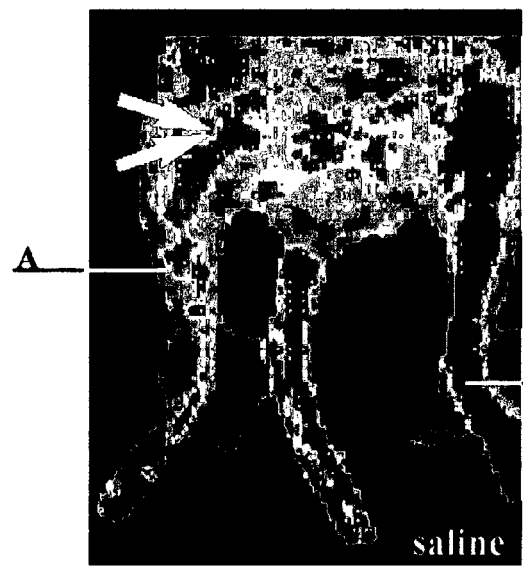
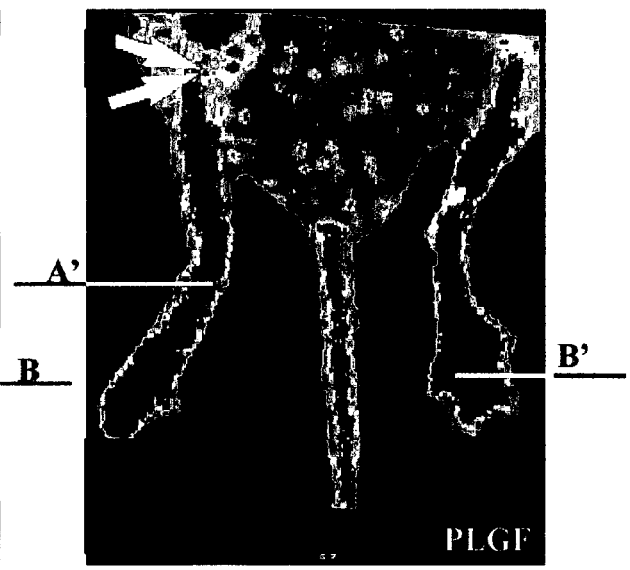
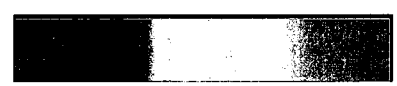
Low flow — High flow
Figure 5
Figure 6

METHOD OF IMPROVING ISCHEMIC MUSCLE FUNCTION BY ADMINISTERING PLACENTAL GROWTH FACTOR

RELATED APPLICATIONS

This application is the non-provisional filing of provisional application No. 60/386,116, filed, Jun. 4, 2002. This application is also a continuation-in-part of U.S. patent application Ser. No. 10/182,359, filed Sep. 23, 2002 (now U.S. Pat. No. 6,930,089), which is the national filing of international application number PCT/EP01/01208 with an international filing date of Feb. 5, 2001.

FIELD OF THE INVENTION

The present invention relates to prevention and treatment of strokes and ischemic diseases and to post-ischemic therapeutic treatment. The invention furthermore relates to the use of a growth factor for treating, more particularly restoring the function of ischemic tissue, in particular muscles such as myocardium and skeletal muscles. The present invention also relates to a method of curing a reduced (e.g. muscular) performance in a mammal, in particular a human being, after an ischemic event. Advantageously the present invention is concerned with the use of a hemodynamically stable medicament which is devoid of side effects associated with other similar growth factors, thus providing specific advantages for hemodynamically compromised patients.

BACKGROUND OF THE INVENTION

Stroke, defined as a sudden weakening or loss of consciousness, sensation and voluntary motion caused by rupture or obstruction of an artery of the brain, is the third cause of death in the United States. Worldwide, stroke is the number one cause of death due to its particularly high incidence in Asia. Ischemic stroke is the most common form of stroke, being responsible for about 85% of all strokes, whereas hemorrhagic strokes (e.g. intraparenchymal or subarachnoid) account for the remaining 15%. Due to the increasing mean age of the population, the number of strokes is continuously increasing. Because the brain is highly vulnerable to even brief ischemia and recovers poorly, primary prevention in ischemic stroke prevention offers the greatest potential for reducing the incidence of this disease.

Focal ischemic cerebral infarction occurs when the arterial blood flow to a specific region of the brain is reduced below a critical level. Cerebral artery occlusion produces a central acute infarct and surrounding regions of incomplete ischemia (sometimes referred to as 'penumbra'), that are dysfunctional-yet potentially salvageable. Ischemia of the myocardium, as a result of reduced perfusion due to chronic narrowing of blood vessels, may lead to fatal heart failure and constitutes a major health threat. Acute myocardial infarction, triggered by coronary artery occlusion, produces cell necrosis over a time period of several hours. In the absence of reflow or sufficient perfusion, the cerebral or myocardial ischemic regions undergo progressive metabolic deterioration, culminating in infarction, whereas restoration of perfusion in the penumbra of the brain infarct or in the jeopardized but salvageable region of the myocardium may ameliorate the tissue damage.

Growth factor mediated improved perfusion of the penumbra in the brain or of the jeopardized myocardium of patients suffering ischemic events, either via increased vasodilation or angiogenesis (the formation of endothelial-lined vessels), may be of great therapeutic value according to Isner et al. in J. Clin. Invest. (1999) 103(9):1231–6 but many questions yet remain to be answered in this respect. This is also true for ischemic conditions related to peripheral limbs (eg peripheral arterial disease, peripheral ischemia). For instance, an outstanding question is whether formation of new endothelial-lined vessels (i.e. angiogenesis) alone is sufficient to stimulate sustainable functional tissue perfusion. Indeed, coverage of endothelial-lined vessels by vascular smooth muscle cells (i.e. arteriogenesis) provides vasomotor control, structural strength and integrity and renders new vessels resistant to regression.

Capillary blood vessels consist of endothelial cells and pericytes, which carry all the genetic information required to form tubes, branches and entire capillary networks. Specific angiogenic molecules can initiate this process. A number of polypeptides which stimulate angiogenesis have been purified and characterized as to their molecular, biochemical and biological properties, as reviewed by Klagsbrun et al. in Ann. Rev. Physiol. (1991) 53:217–239 and by Folkman et al. in J. Biol. Chem. (1992) 267:10931–4. One factor that can stimulate angiogenesis and which is highly specific as a mitogen for vascular endothelial cells, is termed vascular endothelial growth factor (hereinafter referred as VEGF) according to Ferrara et al. in J. Cell. Biochem. (1991) 47:211–218. VEGF is also known as vasculotropin. Connolly et al. also describe in J. Biol. Chem. (1989) 264: 20017–20024, in J. Clin. Invest. (1989) 84:1470–8 and in J. Cell. Biochem. (1991) 47:219–223 a human vascular permeability factor that stimulates vascular endothelial cells to divide in vitro and promotes the growth of new blood vessels when administered into healing rabbit bone grafts or rat corneas. The term vascular permeability factor (VPF for abbreviation) was adopted because of increased fluid leakage from blood vessels following intradermal injection and appears to designate the same substance as VEGF. The murine VEGF gene has been characterized and its expression pattern in embryogenesis has been analyzed. A persistent expression of VEGF was observed in epithelial cells adjacent to fenestrated endothelium, e.g. in chloroid plexus and kidney glomeruli, which is consistent with its role as a multifunctional regulator of endothelial cell growth and differentiation as disclosed by Breier et al. in Development (1992) 114:521–532. VEGF shares about 22% sequence identity, including a complete conservation of eight cysteine residues, according to Leung et al. in Science (1989) 246: 1306–9, with human platelet-derived growth factor PDGF, a major growth factor for connective tissue. Alternatively spliced mRNAs have been identified for both VEGF and PDGF and these splicing products differ in their biological activity and receptor-binding specificity. VEGF is a potent vasoactive protein that has been detected in and purified from media conditioned by a number of cell lines including pituitary cells, such as bovine pituitary follicular cells (as disclosed by Ferrara et al. in Biochem. Biophys. Res. Comm. (1989) 161:851–858 and by Gospodarowicz et al. in Proc. Natl. Acad. Sci. USA (1989) 86: 7311–5), rat glioma cells (as disclosed by Conn. et al. in Proc. Natl. Acad. Sci. USA (1990) 87:1323–1327) and several tumor cell lines. Similarly, an endothelial growth factor isolated from mouse neuroblastoma cell line NB41 with an unreduced molecular mass of 43–51 kDa has been described by Levy et al. in Growth Factors (1989) 2:9–19.

Recent data show that VEGF has a modest effect on collateral growth and limb perfusion measured by microspheres (Deindl et al. in Circ. Res. (2001) 89:779–86), but increases perfusion measured by laser doppler (Isner et al. in Circulation (1999) 99:3188–98). Thus, despite a slight increase in collateral growth and hind limb perfusion, the overall functional reserve after VEGF treatment was impaired, presumably because of unfavorable hemodynamic effects. In other words, it is known that despite vessel formation by means of VEGF, the functionality of the vessels formed is very low. Despite promising initial clinical trials, a large double-blind placebo-controlled trial testing the efficacy of intracoronary and intravenous VEGF for therapeutic angiogenesis in patients with chronic myocardial ischemia not amenable to standard revascularization techniques, indicated that even high dose treatment with VEGF did not lead to a significant improvement in ETT time (Henry et al. 2003, Circulation, 107:1359–1365).

Placental growth factor (hereinafter referred as PlGF) was first disclosed by Maglione et al. in Proc. Natl. Acad. Sci. USA (1991) 88(20):9267–71 as a protein related to the vascular permeability factor. U.S. Pat. No. 5,919,899 discloses nucleotide sequences coding for a protein, named PlGF, which can be used in the treatment of inflammatory diseases and in the treatment of wounds or tissues after surgical operations, transplantations, burns of ulcers and so on. Soluble non-heparin binding and heparin binding forms, built up of 131 and 152 amino-acids and known as PlGF-1 and PlGF-2 respectively, have been described for PlGF and were found to be differentially expressed in placenta, trophoblastic tumors and cultured human endothelial cells (Maglione et al., 1993).

Carmeliet et al. Nat. Med. (2001) 7:575–583 provides an extensive and comprehensive review of the state of the art related to PlGF as follows. VEGF stimulates angiogenesis by activating the VEGF tyrosine kinase receptor-2 (VEGFR-2). Recombinant PlGF stimulates angiogenesis in particular conditions and induces vascular permeability when co-injected with VEGF, but the role of endogenous PlGF remains unknown. Both PlGF and VEGF bind to VEGF receptor-1 (VEGFR-1). PlGF has been proposed to stimulate angiogenesis by displacing VEGF from the 'VEGFR-1 sink', thereby increasing the fraction of VEGF available to activate VEGFR-2. Alternatively, PlGF might stimulate angiogenesis by transmitting intracellular signals through VEGFR-1. PlGF might also affect angiogenesis by forming heterodimers with VEGF, but their role is controversial.

The role of PlGF in angiogenesis was evaluated by inactivating the gene expressing PlGF (Pgf) in mice. Unexpectedly, the absence of PlGF had a negligible effect on vascular development. However, PlGF deficiency reduced pathological angiogenesis, permeability and collateral growth in ischemia, inflammation and cancer.

Carmeliet et al. (cited supra) studied the growth of collateral arteries after ligation of the femoral artery in mice and found that PlGF levels were 45% higher in ligated vessels than in control vessels. On the other hand macrophages, known to play an essential role in collateral growth, infiltrated significantly more collaterals in wild-type mice than in Pgf–/– mice. In another experiment, mice were transplanted with congenic bone marrow and capillary ingrowth in matrigel, supplemented with the VEGF165 isoform, and angiogenesis was quantified by measuring the hemoglobin content per implant. Matrigel angiogenesis was abundant when both the donor bone marrow and the host vessels produced PlGF but minimal when the bone marrow and host lacked PlGF. Capillaries still infiltrated the matrigel in wild-type mice transplanted with Pgf–/– bone marrow, indicating that PlGF production by vessel-wall-associated endothelial cells was sufficient for angiogenesis. When a Pgf–/– recipient was transplanted with wild-type bone marrow, matrigel angiogenesis still occurred, indicating that production of PlGF by bone-marrow cells can stimulate angiogenesis at distant sites. Transplantation of wild-type bone marrow in Pgf–/– mice also rescued the impaired collateral enlargement after ligation of the femoral artery, possibly by mobilizing PlGF-producing monocytes/macrophages to the collaterals. In still another experiment, in order to determine whether the amplification of the VEGF response by PlGF resulted from direct stimulation of endothelial cells, Carmeliet et al. (cited supra) studied capillary outgrowth in intact aortic rings and found that, because PlGF alone (in the absence of VEGF) did not stimulate isolated endothelial cells, PlGF probably stimulated capillary outgrowth by amplifying endogenous VEGF in aortic rings. Carmeliet et al. (cited supra) further observed that even at low doses PlGF dose-dependently restored the impaired VEGF response of Pgf–/– endothelial cells. Further, PlGF activated VEGFR-1. These findings altogether indicate that PlGF, via activation of VEGFR-1, specifically potentiates the angiogenic response to VEGF and that by affecting vascular growth and remodeling, PlGF contributes to the pathogenesis of several disorders with high morbidity.

One problem to be solved by the present invention is to provide a pharmaceutical composition and methods particularly suited for improving perfusion of tissues of patients suffering ischemic events, which will prove to be useful for the prevention and treatment of strokes and ischemic diseases. Another problem to be solved by the present invention is to provide pharmaceutical compositions and methods for reducing or suppressing infarct expansion of the penumbra during ischemic cerebral infarction and for enhancing revascularization of acute myocardial infarcts, making them useful for preventing and treating such events. Another problem to be solved by the present invention is to provide pharmaceutical compositions and methods for enhancing revascularization of tissues in limb-threatening ischemia making them useful for treating such a disease.

Another problem to be solved by the present invention is to provide pharmaceutical compositions and methods not only for enhancing vascularization but for restoring the functionality of ischemic tissue, in particular ischemic muscles such as the cardiac muscle and skeletal muscles in the head, neck, thorax, abdomen, back and upper and lower limbs. There is also a need in the art for curing a reduced physical muscular performance, especially that of heart and the aforesaid muscles after an ischemic event in a mammal, in particular a human being. Another problem to be solved by the present invention is providing a pharmaceutical and methods which can be used as described above without incurring the well known disadvantages of some growth factors such as VEGF, e.g. hypotension after systemic administration of high doses over short periods of time (see for instance Hariawala et al. in J. Surg. Res. (1996) 63(1): 77–82).

SUMMARY OF THE INVENTION

The various above-mentioned goals of the present invention have been successfully and unexpectedly satisfied by a suitable use of placenta growth factor or a fragment, derivative or homologue thereof or alternatively the use of a combination of PlGF and VEGF such as disclosed hereinafter.

The present invention is based on a first unexpected finding that PlGF increases VEGF expression in places where VEGF is already up-regulated, due to ischemic disease conditions, i.e. in places where VEGF is needed. The present invention is also based on a second unexpected finding that PlGF simultaneously stimulates both smooth muscle cells and endothelial cells, whereas VEGF preferentially stimulates endothelial cells. Other observations of the present inventors are that PlGF significantly increases capillary vessel density in muscles, that it is much more efficient than VEGF in stimulating collateral arteriolar growth (for instance in ischemic myocardium or in an ischemic limb). This results in an improved function of the ischemic tissue, more particularly, strongly increased limb motoric function (as could be measured in an endurance swim test). This is corroborated by limb perfusion data showing that, contrary to laser Doppler measurements, perfusion measured by microspheres is quite different in ischemic limbs treated with VEGF and PlGF respectively. PlGF efficiency is thus associated with improved perfusion as a result of constructive angiogenesis, arteriogenesis and collateral vessel growth. These qualities are of particular interest for the restoration of ischemic tissue.

The present invention is further based on the finding that administration of PlGF and VEGF has a synergistic effect in the treatment of in an animal ischemic myocardium and in suppressing infarct expansion of the penumbra.

The present invention is further based on the important finding that treatment with PlGF has less systemic hemodynamic side effects (e.g. loss of blood pressure, edema, hemangioma) than VEGF.

In view of these observations, the present invention first provides the use of PlGF for the treatment and prevention of ischemic disease, and for restoring the function of ischemic tissue in a mammal. The present invention also provides method for curing a reduced physical muscular performance in a mammal after an ischemic event, the said method comprising administering to the said mammal a therapeutically effective amount of a placental growth factor. The present invention also relates to a method of treatment or prevention of a stroke (including a hemorrhagic stroke) or an ischemic disease in a mammal, comprising administering to the mammal in need of such treatment or prevention a therapeutically effective amount of placental growth factor, a fragment, a derivative or a homologue thereof or a combination of PlGF with VEGF.

BRIEF DESCRIPTION OF THE DRAWINGS

FIGS. 3 and 4 show staining of a section through a mouse adductor muscle without treatment and after treatment with hPlGF-2 respectively.

FIGS. 5 and 6 show laser Doppler images of a mouse limb after femoral artery ligation, without treatment and after treatment with hPlGF-2 respectively.

DETAILED DESCRIPTION OF THE INVENTION

Figure 1:
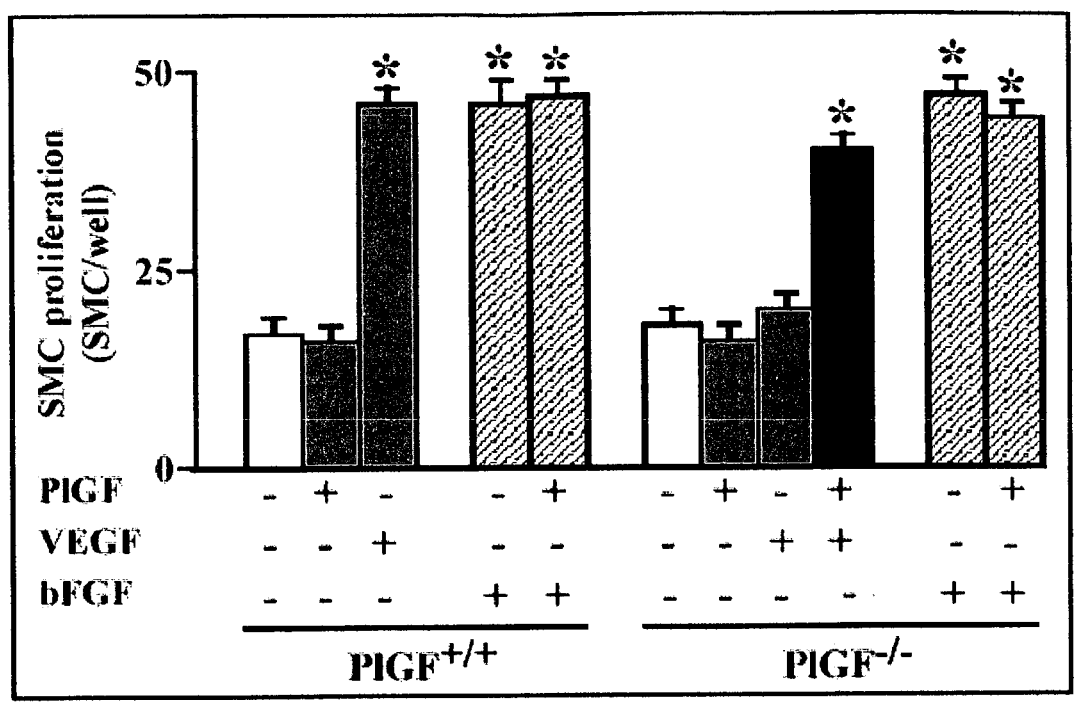
FIG. 1 shows the effects of PlGF, VEGF and bFGF on smooth muscle cells proliferation.

In the present invention "PlGF" should be understood as including all naturally-occurring PlGF isoforms like the 131 and 152 amino-acid isoforms (PlGF-1 and PlGF-2) mentioned above, but also variants having one or more internal deletions or mutations of one or more amino-acids, provided that the said variants have at least 75%, preferably at least 80% and more preferably at least 90%, sequence identity with the aforesaid isoforms. It includes both the full-length protein and modified versions such as N-terminally and/or C-terminally truncated versions of PlGF. The term PlGF relates to both natural and synthetic or recombinant versions of the protein.

A preferred embodiment of PlGF according to the present invention is placental growth factor originating from a mammal or corresponding to a mammalian, preferably a human PlGF. PlGF for use as a medicament or prophylactic to a species preferably originates from the same species or corresponds to a PlGF of the same species (e.g. use of human PlGF for treating humans), although the development of a pharmaceutical of PlGF from one species for treatment of another species is not excluded (e.g. administration of murine, porcine, bovine or primate PlGF to humans).

The term "vascular endothelial growth factor" or "VEGF" as used herein refers, whether of human or animal origin, to all isoforms thereof such as disclosed in the section BACKGROUND OF THE INVENTION. However the 165 amino-acids isoform is preferred.

"bFGF", as used herein relates to basic Fibroblast Growth Factor, is a wide-spectrum mitogenic, angiogenic and neurotrophic factor that is expressed at low levels in many tissues and reaches high concentrations in brain and pituitary.

"ischemia" and "ischemic" is defined herein as a local anemia due to mechanical (e.g. atherosclerotic) obstruction (mainly arterial narrowing or disruption of the blood supply). Examples of ischemic diseases within the scope of this invention include, among others: ischemic stroke or focal ischemic cerebral infarction, acute myocardial infarction or coronary ischemia, chronic ischemic heart disease, ischemic disease of an organ other than myocardium or a region of the brain, for instance a peripheral limb (e.g. limb ischemia or peripheral arterial disease). Accordingly, the ischemic tissue concerned by the present invention may be any tissue of the mammalian body. According to a particular aspect of the invention "ischemic muscles" relates to muscles such as heart (myocardium) and skeletal muscles.

In all of the various aspects of the present invention, the term "mammal" is considered in its common meaning and includes namely humans, equines, felines, canines, porcines, bovines, ovines and the like.

"infarct" herein means any area of necrosis due to a sudden insufficiency of arterial or venous blood supply.

"spontaneous mobility" is defined herein as being the muscle mobility under normal conditions, i.e. without load or stress; examples include the walking at normal speed of a human before occurrence of the ischemic event.

"functional restoration", "functional recovery" and "restoring or restoration of function" all refer to a partial but significant restoration or complete restoration of a functional tissue or muscle reserve of an ischemic tissue. This is determined by comparing the functional efficiency of the tissue after treatment to the functional efficiency of the same tissue immediately prior to and subsequent to the ischemic event in the patient and optionally with reference to the functional efficiency of that tissue in a healthy population. Functional restoration of a muscle tissue is preferably evaluated and/or quantified by means of an endurance exercise test wherein the ischemic tissue or muscle under treatment is put under a physical or load stress condition. Alternatively, the functional restoration is measured by means of an exercise test which reflects the function of the ischemic tissue (e.g. exercise treadmill test for heart function). Most preferably, according to the present invention, restoration obtained by PlGF treatment is at least 30%, more preferably at least 50%, most preferably at least 60%.

"stress condition" refers to a condition significantly more stringent than spontaneous mobility, such as the practice of a sport or physical work involving an effort such as running (as opposed to normal walking), jumping, swimming and the like. The test involved may also include one or more conditions such as load, torsion or similar.

The "hemodynamic side effects" referred to herein relate to disturbances of different aspects of the normal blood flow. More particularly, in the context of the present invention, this relates to (systolic) hypotension, the formation of hemangioma's, edema, ectopic angiogenesis, anemia, neointimal proliferation and renal toxicity. According to a particular aspect of the invention, the absence of one or more side effects upon treatment with a medicament is translated into a preferred use thereof for the treatment of particular disorders, for particular regimens and/or for the treatment of particular patient group, susceptible to the occurrence of such side effects.

A "hemodynamically compromised patient" as used herein refers to a patient with a sub-normal oxygenation of tissues caused for instance by hypotension or severe tachycardia. More particularly, according to one aspect of the present invention, the patient can be defined as having a systolic blood pressure of <100 mm Hg.

A "patient not responsive to VEGF treatment" as used herein refers to a patient in which treatment with VEGF alone (not combined with other growth factors), at doses which do not cause hemodynamic side effects, does not result in significant clinical improvement, more particularly does not result in a significant (and preferably long-term) improvement of the parameters used to measure angiogenic efficacy (such as but not limited to ETT, angina time and angina frequency). An example of such a patient group is described by Henry et al. (2003, Circulation, 107:1359–1365).

By "therapeutically effective amount" is meant an amount of PlGF which produces the desired therapeutic effect in a patient. For example, in reference to a disease or disorder, it is the amount which reduces to some extent one or more symptoms of the disease or disorder, and preferably returns to normal, either partially or completely, physiological or biochemical parameters associated or causative of the disease or disorder. Preferably, according to one aspect of the present invention, the therapeutically effective amount is the amount of PlGF which will lead to a restoration of function of the ischemic tissue. For instance, when used to therapeutically treat a mammal affected by reduced physical muscular performance, it is a daily amount between about 2 μg/kg and 50 mg/kg, preferably between about 0.05 mg/kg and about 2 mg/kg or less than 10 mg/kg, more preferably less than 1 mg/kg body weight of the said mammal. According to the present invention, dosage of PlGF may be significantly higher, can be administered at a higher rate and/or may be administered to a patient for longer periods of time, than can be administered of VEGF without the occurrence of hemodynamic side effects. More particularly, such a dose can be higher than 15 μg/kg/day, up to 100 μg/kg/day and higher. Alternatively, such a dose can be significantly higher than 50 ng/kg/min, including 100 ng/kg/min and higher.

The term "homologue" as used herein with reference to growth factors of the present invention refers to molecules having at least 50%, more preferably at least 70% and most preferably at least 90% amino acid sequence identity with the relevant growth factor.

The term "fragment" as used herein with reference to growth factors of the present invention refers to molecules which contain the active portion of the growth factor, i.e. the portion which is functionally capable of improving perfusion or reducing or suppressing infarct expansion or otherwise enhancing revascularization of infarcts, and which may have lost a number of non-essential (with respect to angiogenesis and/or arteriogenesis) properties of the parent growth factor. Preferably the fragment used in the present invention is the angiogenetic and/or arteriogenetic fragment of the relevant growth factor.

The term "derivative" as used herein with reference to growth factors of the present invention refers to molecules which contain at least the active portion of the growth factor (as defined herein above) and a complementary portion which differs from that present in the wild-type growth factor, for instance by further manipulations such as introducing mutations.

The "sequence identity" of two sequences as used herein relates to the number of positions with identical nucleotides or amino acids divided by the number of nucleotides or amino acids in the shorter of the sequences, when the two sequences are aligned. Preferably said sequence identity is higher than 70%–80%, preferably 81–85%, more preferably 86–90%, especially preferably 91–95%, most preferably 96–100%, more specifically is 100%.

The present invention demonstrates that PlGF is capable of reducing infarct size caused by occlusion of the middle cerebral artery in a mammal and that in doing so, PlGF is as effective as VEGF. Furthermore, in an ischemic mammal, placental growth factor stimulates, better than VEGF, the formation of new endothelial-lined vessels and maturation of these vessels by coverage with vascular smooth muscle cells (arteriogenesis). Thus, according to a first aspect, the present invention provides the use of PlGF for the treatment and prevention of ischemic disease. The present invention thus relates to a method of treatment or prevention of a stroke (including a hemorrhagic stroke) or an ischemic disease in a mammal, comprising administering to the mammal in need of such treatment or prevention a therapeutically effective amount of placental growth factor, a fragment, a derivative or a homologue thereof.

According to this aspect of the invention, PlGF has significant arteriogenic activity upon administration to mammals suffering from ischemic disease. Thus, the present invention is particularly suited for the treatment of patients in need of improved collateral flow to ischemic tissues, e.g. patients with viable but underperfused myocardium as a result of chronic myocardial ischemia, more particularly those patients who are considered unsuitable (on the basis of coronary angiography) for standard revascularization techniques.

The present invention further demonstrates restoration of the function of an ischemic tissue of a mammal upon treatment with PlGF and that this restoration is significantly better than upon treatment with VEGF. Thus, a second aspect of the invention relates to the use of PlGF for restoring the function of ischemic tissue in a mammal. Within this aspect, the following particulars are preferred, but not limitative: the ischemic tissue may be a muscle such as cardiac muscle (myocardium) or a skeletal muscle. The latter may be selected from the musculature of head and neck, the musculature of thorax and abdomen, the musculature of back and the musculature of upper and lower limbs. A non-exhaustive list of skeletal muscles for which the treatment of the invention will be beneficial includes the following: sternocleidomastoid, trapezium, deltoid, pectoralis major, serratus anterior, external oblique abdominal, sartorius, platysma, risorius, depressor anguli oris, depressor labili inferioris, mentalis, orbicularis oris, zygomaticus minor, levator labili superioris, nasalis, zygomaticus major, orbicularis oculi, anterior scalene, levator scapulae, splenius capitis, masseter, auricularis posterior, auricularis superior, auricularis anterior, temporoparietalis, epicranius, semispinalis capitis, triceps brachii, teres major, teres minor, infraspinatus, latissimus dorsi, gluteus maximus, anconeus, extensor carpi ulnaris, extensor digitorum, extensor pollicis longus, extensor retinaculum, dorsal interosseus, adductor pollicis, extensor pollicis brevis, adductor pollicis longus, extensor carpi radialis, brachioradialis, brachialis, piriformis, obturator internus, adductor magnus, semimembranosus, gracilis, semitendinosus, gastronecmius, vastus medialis, rectus femoris, adductor longus, biceps femoris, vastus lateralis, quadriceps femoris, tibialis anterior and peroneus longus.

Preferably, according to this aspect of the invention, the functional restoration of ischemic tissue occurs together with an increased transport of particles or oxygen through arteries and/or veins of the said ischemic tissue, as compared with the corresponding transport before use of the said medicament.

The functional restoration of ischemic tissue can be evaluated in different ways, depending on the tissue concerned. The improvement of function in an ischemic limb is preferably evaluated by means of an endurance exercise test wherein the ischemic tissue under treatment is put under a physical or load stress condition. Alternative assays for measuring function of ischemic tissue are described in the art.

According to this aspect of the invention, the use of PlGF results in a restoration of function. Thus, the present invention is particularly suited for the treatment of patients in need of improved tissue function, e.g. patients reduced heart function. More particularly the use of PlGF is suited for patients not responding to other angiogenic growth factors such as VEGF.

A third aspect of the invention is a method for curing a reduced physical muscular performance in a mammal after an ischemic event, the said method comprising administering to the said mammal a therapeutically effective amount of PlGF. According to this aspect of the invention, PlGF for use in post-ischemic therapeutic treatment is provided.

Preferably, the reduced physical muscular performance to be cured is the performance of a skeletal muscle (e.g. as listed above) or the cardiac muscle.

Preferably, according to this aspect of the invention, curing success is evaluated, preferably quantified by means of an endurance exercise test wherein the ischemic muscle under treatment is put under a physical or load stress condition or by measuring the performance in an exercise test which reflects the function of the ischemic muscle.

A fourth aspect of the invention relates to the use of compositions comprising PlGF and VEGF, as active ingredients in respective proportions such as to provide a synergistic effect in the prevention or treatment of strokes and ischemic diseases in mammals. In view of the hemodynamic side-effects observed with higher doses of VEGF, the combination of VEGF with a growth factor which not only provides a synergistic effect but moreover does not to the same extent cause these side effects may be of particular value for the treatment or prevention of particular diseases, or for a particular patient group.

According to the present invention, a medicament is provided for the treatment and prevention of ischemic disease, which does not significantly cause the hemodynamic side-effects of other known growth factors. More particularly, it is demonstrated that the treatment of an ischemic mammal with PlGF has a much more limited effect on systolic blood pressure and causes less edema than VEGF, which may be of use for the patients in need thereof. Thus, according to a fourth aspect of the present invention, the use of PlGF is provided for the treatment of patients who are particularly susceptible to hemodynamic side-effects or are hemodynamically compromised or who are not responsive to VEGF, most particularly those patients not responding positively to high doses of VEGF. Moreover, the present invention provides the use of placental growth factor, where prolonged treatment is required, e.g. for the treatment of chronic ischemic diseases.

The present invention furthermore relates to the manufacture of a medicament for the treatment and prevention of the conditions and diseases described above.

In the methods of treatment or prevention constituting various aspects of the present invention, the administration of active ingredient(s) may be chronic or intermittent, depending on the medical status and need of the mammal. According to one aspect of the present invention, the mammal particularly suited for the treatment with PlGF is a mammal suffering from an ischemic disease, particularly in cases where standard revascularization techniques are not advisable. Treatment of mammals with myocardial ischemia with PlGF in the context of the present invention is envisaged both immediately after myocardial infarction and up to or starting from a period thereafter, including 6 months after infarction.

In the various aspects of the present invention where both placenta growth factor and vascular endothelial growth factor are present as biologically active ingredients (a) and (b) respectively, they are preferably used as a combined preparation comprising from about 1 to about 99% by weight of ingredient (a) and from about 1 to about 99% by weight of ingredient (b) for simultaneous, separate or sequential use. In view of the fact that ingredients (a) and (b) do not necessarily bring out their joint therapeutic effect directly at the same time in the mammal to be treated or prevented, the pharmaceutical compositions of the present invention which comprise both ingredients (a) and (b) may be in the form of a medical kit or package containing the two ingredients in separate but adjacent form. In the latter context, each of ingredients (a) and (b) may therefore be formulated in a way suitable for an administration route different from that of the other ingredient.

The optimal formulation and mode of administration of PlGF (optionally combined with VEGF) to a patient depend on factors known in the art such as the particular disease or disorder, the desired effect, and the type of patient. Preferably, the therapeutically effective amount is provided as a pharmaceutical or veterinary composition. Suitable forms in part depend upon the mode of administration, for example oral, transdermal, or by injection into the blood stream. Such forms should allow PlGF to efficiently reach the target cells. For example, pharmacological compositions injected into the blood stream should be soluble. Other factors are known in the art, and include considerations such as toxicity and forms which would prevent the composition from exerting its effect.

In the pharmaceutical compositions constituting various aspects of the present invention, the term "pharmaceutically acceptable carrier" means any material or substance with which the active ingredient(s) is formulated in order to facilitate its application or dissemination, for instance by dissolving, dispersing or diffusing the said ingredient, and/or to facilitate its storage, transport or handling without impairing its effectiveness. The pharmaceutically acceptable carrier may be a solid or a liquid or a gas which has been compressed to form a liquid, i.e. the compositions of this invention can suitably be used as concentrates, emulsions, solutions, granulates, dusts, sprays, aerosols, pellets or powders. However a formulation suitable for subcutaneous use is highly preferred.

Suitable pharmaceutical carriers for use in the present compositions are well known to those skilled in the art, and there is no particular restriction to their selection within the invention. They may also include additives such as wetting agents, dispersing agents, stickers, adhesives, emulsifying agents, solvents, coatings, antibacterial and antifungal agents (for example phenol, sorbic acid, chlorobutanol), isotonic agents (such as sugars or sodium chloride) and the like, provided the same are consistent with pharmaceutical practice, i.e. carriers and additives which do not create permanent damage to mammals. The pharmaceutical compositions of the present invention may be prepared in any known manner, for instance by homogeneously mixing, coating and/or grinding the active ingredients, in a one-step or multi-steps procedure, with the selected carrier material and, where appropriate, the other additives such as surface-active agents may also be prepared by micronisation, for instance in view to obtain them in the form of microspheres usually having a diameter of about 1 to 10 μm, namely for the manufacture of microcapsules for controlled or sustained release of the active ingredients.

Suitable surface-active agents to be used in the pharmaceutical compositions of the present invention are non-ionic, cationic and/or anionic materials having good emulsifying, dispersing and/or wetting properties. Suitable anionic surfactants include both water-soluble soaps and water-soluble synthetic surface-active agents. Suitable soaps are alkaline or alkaline-earth metal salts, unsubstituted or substituted ammonium salts of higher fatty acids (C10–C22), e.g. the sodium or potassium salts of oleic or stearic acid, or of natural fatty acid mixtures obtainable form coconut oil or tallow oil. Synthetic surfactants include sodium or calcium salts of polyacrylic acids; fatty sulphonates and sulphates; sulphonated benzimidazole derivatives and alkylarylsulphonates. Fatty sulphonates or sulphates are usually in the form of alkaline or alkaline-earth metal salts, unsubstituted ammonium salts or ammonium salts substituted with an alkyl or acyl radical having from 8 to 22 carbon atoms, e.g. the sodium or calcium salt of lignosulphonic acid or dodecylsulphonic acid or a mixture of fatty alcohol sulphates obtained from natural fatty acids, alkaline or alkaline-earth metal salts of sulphuric or sulphonic acid esters (such as sodium lauryl sulphate) and sulphonic acids of fatty alcohol/ethylene oxide adducts. Suitable sulphonated benzimidazole derivatives preferably contain 8 to 22 carbon atoms. Examples of alkylarylsulphonates are the sodium, calcium or alcanolamine salts of dodecylbenzene sulphonic acid or dibutyl-naphtalenesulphonic acid or a naphtalene-sulphonic acid/formaldehyde condensation product. Also suitable are the corresponding phosphates, e.g. salts of phosphoric acid ester and an adduct of p-nonylphenol with ethylene and/or propylene oxide, or phospholipids. Suitable phospholipids for this purpose are the natural (originating from animal or plant cells) or synthetic phospholipids of the cephalin or lecithin type such as e.g. phosphatidylethanolamine, phosphatidylserine, phosphatidylglycerine, lysolecithin, cardiolipin, dioctanylphosphatidyl-choline, dipalmitoylphoshatidyl-choline and their mixtures.

Suitable non-ionic surfactants include polyethoxylated and polypropoxylated derivatives of alkylphenols, fatty alcohols, fatty acids, aliphatic amines or amides containing at least 12 carbon atoms in the molecule, alkylarenesulphonates and dialkylsulphosuccinates, such as polyglycol ether derivatives of aliphatic and cycloaliphatic alcohols, saturated and unsaturated fatty acids and alkylphenols, said derivatives preferably containing 3 to 10 glycol ether groups and 8 to 20 carbon atoms in the (aliphatic) hydrocarbon moiety and 6 to 18 carbon atoms in the alkyl moiety of the alkylphenol. Further suitable non-ionic surfactants are water-soluble adducts of polyethylene oxide with poylypropylene glycol, ethylenediaminopolypropylene glycol containing 1 to 10 carbon atoms in the alkyl chain, which adducts contain 20 to 250 ethyleneglycol ether groups and/or 10 to 100 propyleneglycol ether groups. Such compounds usually contain from 1 to 5 ethyleneglycol units per propyleneglycol unit. Representative examples of non-ionic surfactants are nonylphenol-polyethoxyethanol, castor oil polyglycolic ethers, polypropylene/polyethylene oxide adducts, tributylphenoxypolyethoxyethanol, polyethyleneglycol and octylphenoxypolyethoxyethanol. Fatty acid esters of polyethylene sorbitan (such as polyoxyethylene sorbitan trioleate), glycerol, sorbitan, sucrose and pentaerythritol are also suitable non-ionic surfactants.

Suitable cationic surfactants include quaternary ammonium salts, preferably halides, having 4 hydrocarbon radicals optionally substituted with halo, phenyl, substituted phenyl or hydroxy; for instance quaternary ammonium salts containing as N-substituent at least one C8–C22 alkyl radical (e.g. cetyl, lauryl, palmityl, myristyl, oleyl and the like) and, as further substituents, unsubstituted or halogenated lower alkyl, benzyl and/or hydroxy-lower alkyl radicals.

A more detailed description of surface-active agents suitable for this purpose may be found for instance in "McCutcheon's Detergents and Emulsifiers Annual" (MC Publishing Crop., Ridgewood, N.J., 1981), "Tensid-Taschenbuch", 2ed. (Hanser Verlag, Vienna, 1981) and "Encyclopaedia of Surfactants (Chemical Publishing Co., New York, 1981).

Additional ingredients may be included in order to control the duration of action of the active ingredient in the pharmaceutical composition of the invention. Control release compositions may thus be achieved by selecting appropriate polymer carriers such as for example polyesters, polyamino acids, polyvinyl pyrrolidone, ethylene-vinyl acetate copolymers, methylcellulose, carboxymethylcellulose, protamine sulfate and the like. The rate of drug release and duration of action may also be controlled by incorporating the active ingredient into particles, e.g. microcapsules, of a polymeric substance such as hydrogels, polylactic acid, hydroxymethylcellulose, polymethyl methacrylate and the other above-described polymers. Such methods include colloid drug delivery systems like liposomes, microspheres, microemulsions, nanoparticles, nanocapsules and so on.

Carriers or excipients may be used to facilitate administration of PlGF. Examples of suitable carriers and excipients include fillers, various sugars such as lactose, glucose, sucrose, starch, cellulose derivatives, gelatin, vegetable oils, polyethylene glycols and physiologically compatible solvents.

PlGF may be formulated in solid form and dissolved or suspended immediately prior to use. Lyophilized forms for the extemporaneous preparation also included.

The pharmaceutical (or veterinary) composition of the present invention may be administered by different routes including intravenously, intraperitoneally, subcutaneously, intramuscularly, orally, topically or transmucosally. PlGF may be formulated for either systemic or localized administration. Techniques and formulations generally may be found in Remington's Pharmaceutical Sciences (1990), 18$^{th}$ ed., Mack Publishing Co., Easton, Pa. A suitable administration form may best be determined by a medical practitioner for each patient individually.

For systemic administration, injection is preferred. Typical carriers for this purpose therefore include biocompatible aqueous buffers (such as Hank's solution or Ringer's solution) and excipients being generally accepted as safe as defined by USP standards (e.g., ethanol, glycerol, propylene glycol, polyethylene). It can e.g. be suspended in an inert oil, suitably a vegetable oil such as sesame, peanut, olive oil, or other acceptable carrier. Preferably, it suspended in an aqueous carrier, for example, in an isotonic buffer solution at a pH of about 5.6 to 7.4. These compositions may be sterilized by conventional sterilization techniques, or may be sterile filtered. They may contain pharmaceutically acceptable auxiliary substances as required to approximate physiological conditions, such as pH buffering agents. Useful buffers include for example, sodium acetate/acetic acid buffers.

Systemic administration can also be by transmucosal or transdermal means or orally. For transmucosal or transdermal administration, penetrants appropriate to the barrier to be permeated are used in the formulation. Such penetrants are generally known in the art, and include, for example, for transmucosal administration, bile salts and fusidic acid derivatives. In addition, detergents may be used to facilitate permeation. Transmucosal administration may be through nasal sprays or suppositories. For oral administration, the therapeutically active substance is formulated into conventional oral administration dosage forms such as capsules, tablets or liquid preparations.

For topical administration, PlGF may be formulated into ointments, gels or creams as is generally known in the art. If desired the above compositions may be thickened with a thickening agent such as methylcellulose. They may be prepared in emulsified form, either water in oil or oil in water. Any of a wide variety of pharmaceutically acceptable emulsifying agents may be employed including, for example, acacia powder, a non-ionic surfactant (such as Tween®), or an ionic surfactant (such as an alkali polyether alcohol sulfate or sulfonate, e.g. Triton®).

Pharmaceutical or veterinary compositions useful in the invention may be prepared by mixing the above-mentioned ingredients following generally accepted procedures. For example, the said ingredients may be simply mixed in a blender or other standard device to produce a concentrated mixture which may then be adjusted to the final desired concentration and viscosity by the addition of water and/or a thickening agent and possibly a buffer to control pH or an additional solute to control tonicity.

PlGF may also be used according to gene therapy methods well known in the art. For instance, an expression vector containing the PlGF coding sequence may be inserted into cells, the said cells are grown in vitro and then injected or infused into the patient. In another example, a DNA segment containing a promoter (e.g. a strong promoter) is transferred into cells containing an endogenous PlGF in such a manner that the promoter segment enhances expression of the endogenous PlGF gene. The gene therapy method may also involve the use of an adenovirus vector including a nucleotide sequence coding for PlGF or a naked nucleic acid molecule coding for a PlGF subunit. Alternatively, engineered cells containing a nucleic acid molecule coding for a PlGF subunit may be injected. Expression vectors derived from viruses such as retroviruses, vaccinia virus, adenovirus, adeno-associated virus, herpes viruses, RNA viruses or bovine papilloma virus, may be used for delivery of nucleotide sequences (e.g., cDNA) encoding recombinant PlGF subunit into the targeted cell population. Methods which are well known to those skilled in the art can be used to construct recombinant viral vectors containing such coding sequences.

Alternatively, recombinant nucleic acid molecules encoding protein sequences can be used as naked DNA or in liposomes or other lipid systems for delivery to target cells. Other methods for the direct transfer of plasmid DNA into cells are well known to those skilled in the art for use in human gene therapy and involve targeting the DNA to receptors on cells by complexing the plasmid DNA to proteins. In its simplest form, gene transfer can be performed by simply injecting minute amounts of DNA into the nucleus of a cell, through a process of microinjection. Once recombinant genes are introduced into a cell, they can be recognized by the cells normal mechanisms for transcription and translation, and a gene product will be expressed. Other methods have also been attempted for introducing DNA into larger numbers of cells. These methods include: transfection, wherein DNA is precipitated with calcium phosphate and taken into cells by pinocytosis; electroporation, wherein cells are exposed to large voltage pulses to introduce holes into the membrane); lipofection/liposome fusion, wherein DNA is packed into lipophilic vesicles which fuse with a target cell; and particle bombardment using DNA bound to small projectiles. Another method for introducing DNA into cells is to couple the DNA to chemically modified proteins. Adenovirus proteins are capable of destabilizing endosomes and enhancing the uptake of DNA into cells. Mixing adenovirus to solutions containing DNA complexes, or the binding of DNA to polylysine covalently attached to adenovirus using protein crosslinking agents substantially improves the uptake and expression of the recombinant gene. Adeno-associated virus vectors may also be used for gene delivery into vascular cells. As used herein, "gene transfer" means the process of introducing a foreign nucleic acid molecule into a cell, which is commonly performed to enable the expression of a particular product encoded by the gene. The said product may include a protein, polypeptide, anti-sense DNA or RNA, or enzymatically active RNA. Gene transfer can be performed in cultured cells or by direct administration into mammals.

In another embodiment, a vector having nucleic acid molecule sequences encoding PlGF is provided in which the nucleic acid molecule sequence is expressed only in a specific tissue. Methods of achieving tissue-specific gene expression are well known in the art. In yet another embodiment, a method of gene replacement is set forth. "Gene replacement" as used herein means supplying a nucleic acid molecule sequence which is capable of being expressed in vivo in a mammal and thereby providing or increasing the function of an endogenous gene which is missing or defective in the said mammal.

The present invention will now be illustrated by means of the following examples which are provided without any limiting intention.

EXAMPLES

Experimental Methods

VEGF and PlGF protein levels were quantified by ELISA (R&D Systems, Abingdon, UK). rhVEGF$_{165}$ was available from R&D Systems and rhPlGF-2 from Gaymonat, Spa, Anagni, Italy or from Reliatech (Braunschweig, Germany). It was observed that PlGF obtained from different sources had different specific activity. Nevertheless, the relative safety of PlGF over VEGF was always confirmed, indicating that a dosage of PlGF of more than 15 µg/kg/day of active ingredient up to 100 µg/kg/day or higher could be administered without the occurrence of hemodynamic side effects.

Animal experiments were conducted according to the guiding principles of the American Physiological Society and the International Committee on Thrombosis and Haemostasis as published by A. Giles in Thromb. Haemost. (1987) 58:1078–1084.

For isolation of smooth muscle cells (SMCs), media fragments of the aorta were incubated for 16 h at 37° C. in DMEM containing 0.15% collagenase, 5% fetal calf serum (FCS) and antibiotics. After incubation, SMCs were sedimented by centrifugation (400 g; 10 min), resuspended in DMEM+10% FCS and grown at 37° C. in a humidified atmosphere of 5% CO2 in air. Cells were routinely used from the third to the sixth passage. Proliferation of SMCs was studied. Generation of mice knock-outs for PlGF (Pgf-/-) was performed as described in Cameliet al. 2001, Nature Med, 7(5):575–583.

Mouse Model of Focal Cerebral Ischemia

Focal cerebral ischemia was produced by persistent occlusion of the MCA according to Welsh et al. in J. Neurochem. (1987) 49:846–51. Briefly, mice 10 of either sex weighing 20 to 30 g, with a genetic background of 50% Swiss/50% 129 were anesthetized by intraperitoneal injection of ketamine (75 mg/ml, available from Apharmo, Arnhem, Netherlands) and xylazine (5 mg/ml, available from Bayer, Leverkusen, Germany). Atropine (1 mg/kg, available from Federa, Brussels, Belgium) was administered intramuscularly and body temperature was maintained by keeping the animals on a heating pad. A "U" shape incision was made between the left ear and left eye. The top and backside segments of the temporal muscle were transsected and the skull was exposed by retraction of the temporal muscle. A small opening (1 to 2 mm diameter) was made in the region over the MCA with a hand-held drill, with saline superfusion to prevent heat injury. The meningae were removed with a forceps and the MCA was occluded by ligation with 10–0 nylon thread (available from Ethylon, Neuilly, France) and transsected distally to the ligation point. Finally, the temporal muscle and skin were sutured back in place. The animals were allowed to recover and were then returned to their cages. Infarcted mice were treated with saline (for control) or growth factors using an osmotic minipump (Alzet type 2001, Broekman Institute, Someren, Netherlands), subcutaneously implanted on the back, so that the growth factors were continuously delivered over a period of 7 days. After that period, the animals were sacrificed with an overdose of Nembutal (500 mg/kg, available from Abbott Laboratories, North Chicago, Ill.), perfusion fixed via the left ventricle with 4% formalin in phosphate buffer saline, and decapitated. The brain was removed, processed for histology as described by P. Carmeliet et al. in Nature (1996) 380: 435439, Nature (1996) 383:73–75 and Nature (1998) 394: 485490 and immune-stained for microtubule-associated protein-2 (hereinafter referred as MAP2), a structural protein that disappears early during irreversible ischemic death. MAP-2 negative infarct areas throughout the brain were morphometrically quantified at 420 [mu]m distances using a dedicated image analysis system (Quantimed 6000, available from Leica). The infarct volume was defined as the sum of the unstained areas of the sections multiplied with their thickness.

Mouse Model of Myocardial and Limb Ischemia

In order to induce limb ischemia, unilateral right or bilateral ligations of the femoral artery and vein (proximal to the popliteal artery) and the cutaneous vessels branching from the caudal femoral artery side branch were performed without damaging the nervus femoralis. Then a subcutaneously implanted osmotic minipump (Alzet, type 2001, available from Iffa Credo, Belgium) continuously delivered during 7 days a daily dose of growth factors or saline. Two superficial preexisting collateral arterioles, connecting the femoral and saphenous artery, were used for analysis.

Functional perfusion measurements of the collateral region were performed using a Lisca PIM II camera (available from Gambro, Breda, The Netherlands) and analyzed as decribed in Couffinhal et al., Am. J. Pathol. (1998) 152: 1667–79. Perfusion, averaged from three images per mouse in the upper hind limb (adductor region where collaterals enlarge) or in total hind limb, was expressed as a ratio of right (ischemic) to left (normal) limb. Spontaneous mobility was scored by monitoring the gait abnormalities, the position of right foot in rest and after manipulation, and the "tail-abduction-reflex". Mice were scored 0 when one observation was abnormal and 1 when normal.

Restoration of muscle function was tested by way of a physical stress test. An endurance exercise swim test for mice was developed. Mice were conditioned to swim in a 31° C. temperature controlled swimming pool for 9 days in non-stressed conditions. At day 10, baseline exercise time for each mouse was determined using a counter-current swimming pool (flow at 0.2 m/s), as disclosed by Matsumoto et al. in J. Appl. Physiol. (1996) 81:1843–9. For determining maximal endurance exercise, the total swimming period until fatigue, defined as the failure to rise to the surface of the water to breathe within 7 seconds, was assessed. At day 11, the femoral artery was occluded, and at day 18, minipumps were removed under isoflurane anesthesia prior to endurance exercise. Recovery of functionality was expressed as a ratio to the baseline exercise time.

Hind-limb perfusion was measured as follows: fluorescent microspheres (yellow-green, 15 µm, 1×106 beads/ml, available from Molecular Probes) were administered after maximal vasodilation (sodium nitroprusside, 50 ng/ml, Sigma) and flow was calculated as described by Carmeliet et al. in Nat. Med. (1999) 5:495–502. Bismuth gelatino-angiography was performed as described by Carmeliet et al. (cited supra)

Collateral arterioles were identified by photo-angiographs (obtained with a Nikon D1 digital camera) analyzed in a blinded manner. Collateral side is branches were categorized as follows: second generation collateral arterioles directly branched off from the main collateral, while third generation collateral arterioles were orientated perpendicularly to the second generation branches. The number of collateral branches per cm length of the primary collateral arteriole was counted.

Fluoroangiography was performed as follows. Images were reconstructed with a Zeiss LSM510 confocal laser microscope. After perfusion-fixation, the two superficial collateral arterioles were post-fixed in paraformaldehyde 1% and paraffin-embedded. Twelve 5 µm cross-sections per superficial collateral, starting from the mid-zone and ranging over 1.95 mm to each end were morphometrically analyzed. Collateral side branches were categorized as second generation (luminal area above 300 µm$^2$) or third generation (below 300 µm$^2$). Total perfusion area was calculated using the total sum of the side branch luminal areas.

Capillary density was determined by immuno-staining for thrombomodulin. Wall thickness of fully small muscle cells (SMC)-covered vessels was morphometrically measured on histological sections, after smooth muscle alpha-actin staining. For all treatment groups, six cross-sections (150 µm apart) were analyzed per main collateral. Only second-generation collateral arterioles larger than 300 µm$^2$ were included in the analysis (see Table 4). At least ten measurements of wall thickness of the second generation collateral arterioles were obtained.

Example 1

Protection Against Cerebral Ischemic Infarct Expansion by Chronic Administration of PlGF Infarcted mice were treated with saline (for control), PlGF (715 ng/day) or VEGF days (425 ng/day) or a combination of both. The data of these experiments, presented in Table 1 below, are the mean+-standard error of mean (SEM) values of the infarct size expressed in mmand used as a means for measuring cerebral infarction, including the number of observations between brackets and wherein an asterisk means p=0.001 vs. control. The significance of differences was determined by unpaired t-test. Intracerebral bleeding was not observed in any of the mice. These data indicate that PlGF is as effective as PlGF in suppressing infarct expansion of the penumbra. These data also indicate that there is a synergistic effect of VEGF and PlGF in suppressing infarct expansion of the penumbra

TABLE 1

| Treatment group | Infarct size |
| --- | --- |
| Control | 12 ± 1.7 (7) |
| PlGF | 8.0 ± 2.9 (4) |
| VEGF | 7.6 ± 2.5 (3) |
| PlGF + VEGF | 4.6 ± 1.3 (8) |

Example 2

Enhanced Revascularization of Acute Myocardial Infarcts by Chronic Administration of PlGF The therapeutic effect of PlGF and VEGF was compared in a murine model for acute myocardial infarction by delivering the growth factors continuously over 7 days. Treatment of infarcted mice with PlGF (715 ng/day or 3.5 µg/day) was more effective than VEGF (450 ng/day) in improving myocardial angiogenesis and arteriogenesis, as shown in Tables 2 and 3 Moreover, a synergistic effect of PlGF and VEGF can be observed, especially in the formation of medium and large vessels. Table 2 provides the number of vessels (mean±SEM values), identified by thrombomodulin staining of endothelial cells as a measure of angiogenesis, throughout the infarct in groups of 8 to 10 mice each. An asterisk means p<0.05 vs. control. Table 3 provides the number of vessels (mean±SEM values), identified by smooth muscle alpha-actin staining of endothelial cells as a measure of arteriogenesis, throughout the infarct in groups of 8 to 10 mice each. An asterisk means p<0.05 vs. control.

TABLE 2

| | Vessels per infarct | | |
| --- | --- | --- | --- |
| Growth factor | Small vessels | Medium vessels | Large vessels |
| Control | 225 ± 20 | 50 ± 4 | 33 ± 3 |
| PlGF (715 ng/24) | 500 ± 45* | 81 ± 7* | 47 ± 4* |
| PlGF (3.5 µg/24 h) | 410 ± 50* | 115 ± 19* | 61 ± 6* |
| VEGF (450 ng/24 h) | 370 ± 40* | 85 ± 7* | 42 ± 2* |
| PlGF (715 ng/24 h) + VEGF (450 ng/24 h) | 470 ± 100* | 110 ± 8* | 67 ± 3* |

TABLE 3

| | Vessels per infarct | | |
| --- | --- | --- | --- |
| Growth factor | Small vessels | Medium vessels | Large vessels |
| Control | 88 ± 4 | 17 ± 2 | 11 ± 2 |
| PlGF (715 ng/24 h) | 140 ± 36* | 30 ± 7* | 14 ± 3* |
| PlGF (3.5 µg/24 h) | 120 ± 18* | 44 ± 10* | 19 ± 3* |
| VEGF (450 ng/24 h) | 104 ± 19* | 26 ± 5* | 11 ± 2 |
| PlGF (715 ng/24 h) + VEGF (450 ng/24 h) | 111 ± 7* | 38 ± 4* | 22 ± 2* |

It was also found that PlGF stimulates myocardial angiogenesis by increasing VEGF expression by fibroblasts, which are abundant in the myocardial stroma. The following expression levels were detected:

<10 pg/ml per 10$^6$ cells per 24 hours after saline, versus 1500 pg/ml per 10$^6$ cells per 24 hours after 100 ng/ml hPlGF-2.

The direct effect of PlGF on arteriogenesis i.e. the maturation of vessels via coverage with smooth muscle cells (SMC) leading to stabilization and durability of new vessels was also investigated. It was found that in the ischemic mouse model rhPlGF-2 stimulated arteriogenesis, since 30% of the new myocardial vessels stained positively for the SMC alpha-actin marker after treatment with all PlGF isoforms. A similar fraction (25%) of myocardial vessels is normally covered by SMC, indicating that PlGF did not (contrary to VEGF, see Carmeliet in Nat. Med. (2000) 6:1102–3) cause the formation of hemangiomas but created a new myocardial vasculature with normal characteristics. The functionality of the new vasculature was evidenced by the improved perfusion of the ischemic myocardium after PlGF treatment (1300 µl/min.g after saline versus 2100 µl/min.g after hPlGF-2 as determined by microspheres).

PlGF determined the responsiveness of SMC to VEGF, since PlGF-/-SMC only proliferated normally in response to VEGF when PlGF was present. As evidenced by FIG. 1, PlGF did not affect wild-type SMC, because their response to exogenous PlGF was obscured by endogenous PlGF production. On the left part of FIG. 1, it is shown on the one hand that VEGF stimulates proliferation of wild type (PlGF+/+) small muscle cells (SMC) at similar levels as bFGF, and on the other hand that PlGF is ineffective in modulating the effect of bFGF. On the right part of FIG. 1, it is shown that VEGF fails to induce growth of PlGF deficient (PlGF-/-) SMC while PlGF, although being ineffective by itself, amplifies the mitogenic response to VEGF.

This synergism between VEGF and PlGF is specific, since PlGF failed to enhance bFGF-induced SMC proliferation.

Example 3

PlGF Delivery Did Not Cause Side Effects

At the dose of 1.5 μg, administered daily for 7 days PlGF did not cause oedema or ectopic angiogenesis in the mouse model for acute myocardial infarction, while local signs of oedema were clearly present around the mini-pumps delivering VEGF. PlGF plasma levels up to about 50 ng/ml (achieved by the delivery of 7 μg hPlGF-2 per day for 7 days) were well tolerated without any sign of distress, while VEGF plasma levels above 10 ng/ml caused severe life threatening signs of oedema and circulatory shock. On the other hand, unlike VEGF, PlGF only minimally affected the blood pressure. Mean arterial blood pressure (measured using high fidelity pressure micromanometers, Miller Instruments, Houston, Tex.) was 93±5 mm Hg under baseline conditions (control mice). Intravenous bolus injection of 3 μg VEGF caused significant hypotension (68±3 mm Hg; $p<0.05$), while 5 to 10 μg hPlGF-2 did not significantly reduce arterial blood pressure (91±11 mm Hg). Thus, PlGF effectively stimulates angiogenesis in the ischemic myocardium, but with the absence of hemodynamic side effects such as oedema or hypoxia.

Example 4

PlGF Restores the Function of Ischemic Skeletal Muscles

The therapeutic effect of PlGF and VEGF was further compared in a murine model for hind-limb ischemia by delivering the growth factors continuously over 7 days at a dose of 1.5 μg of rhVEGF165 or rhPlGF-2 (in quantities expressed as active dimer). In contrast to its angiogenic effect in the ischemic heart, VEGF has only a very limited arteriogenic activity in the ischemic limb and, unlike PlGF, did not induce the same favourable structural and perfusional changes as PlGF. Especially the microsphere measurements, which more reliably assessed perfusion in the affected muscle than laser doppler measurements and are not influenced by vasodilation in the skin, revealed that hind limb perfusion was not as much increased by VEGF treatment as by PlGF treatment, as shown in Table 4.

As can be seen from Table 4, perfusion with PlGF both significantly improved the spontaneous hind limb mobility and restored hind limb function to 67% (as opposed to 36% restoration by saline) as measured by the swim test. VEGF treatment improved the spontaneous hind limb mobility but VEGF-treated mice were much weaker and performed significantly worse in the swim endurance test (Table 4). Thus, despite a slight increase in collateral vessel growth and hind limb perfusion, the overall functional reserve after VEGF treatment was impaired, presumably because of unfavourable hemodynamic effects.

TABLE 4

|  | Saline | PlGF | VEGF |
|---|---|---|---|
| Mean collateral lumen area (μm²) | | | |
| Collateral arteriole | 1760 | 1710 | 1700 |
| Second-generation collateral side branch | 550 | 830 | 610 |
| Third-generation collateral side branch | 130 | 160 | 150 |
| Collateral side branches (photoangiography) | | | |
| 2nd generation collateral side branches (n/cm) | 21 | 36 | 21 |
| 3rd generation collateral side branches (n/cm) | 43 | 65 | 40 |
| Secondary and tertiary collateral branches | | | |
| % Mice with > 30% of collaterals > 300 μm² | 36 | 86 | 44 |
| Total perfusion area (μm²/mm²) | 2670 | 3900 | 2300 |
| Capillary density in adductor muscle (n/mm²) | 3100 | 2800 | 3600 |
| Limb perfusion | | | |
| Laser doppler (% of non-ligated) | | | |
| -Total hindlimb | 61 | 89 | 90 |
| -Upper hindlimb | 83 | 100 | 100 |
| Microspheres (ml.g − 1.min − 1) | | | |
| -Adductor muscle (collateral region) | 0.06 | 0.22 | 0.13 |
| -Gastrocnemeus muscle | 0.12 | 0.35 | 0.21 |
| Limb motoric function | | | |
| Spontaneous mobility (score 0–1) | 0.71 | 1 | 1 |
| Swim test (% of baseline) | 36 | 67 | 18 |

Example 5

PlGF Stimulates Arteriogenesis in Ischemic Limbs

Figure 2:
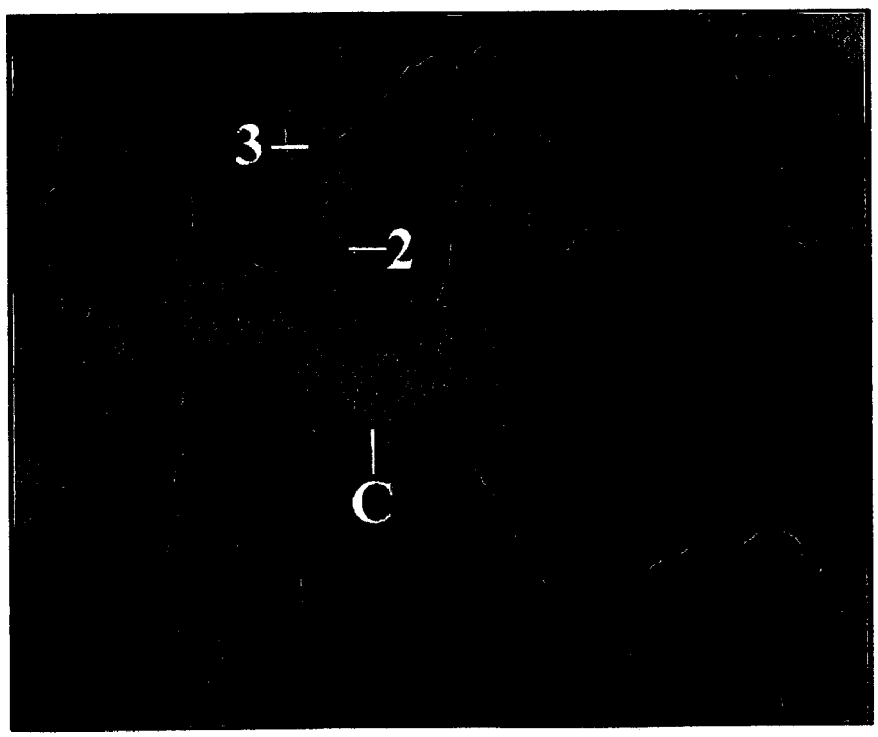
FIG. 2 is a fluoroangiography picture of the adductor region of a mouse treated with PlGF after ligation of the femoral artery.

The ability of PlGF to stimulate the growth of pre-existing arterial collaterals and their second generation and third generation side branches (collateral growth) was evaluated by treating mice with PlGF after ligation of their femoral artery. The development of a primary collateral artery (C) with secondary (2) and tertiary (3) collateral side branches could be determined by fluoroangiography (FIG. 2). Delivery of 1.5 μg hPlGF-2 per day minimally affected the primary collaterals and capillaries in the adductor muscle region, but significantly increased the number and size of the second generation and third generation collateral branches, thereby enlarging the collateral perfusion area (i.e. the sum of luminal areas of all secondary and tertiary collateral vessels, see Table 4). FIG. 4 (wherein the magnification bar represents 50 μm) shows a hematoxylin-eosin staining of a section through the adductor muscle, wherein the lumen of the collaterals is filled with dark bismuth gelatin, revealing enlarged collateral side branches (arrowheads) after hPlGF-2 treatment, as compared to control (FIG. 3). PlGF treatment increased the number of precapillary arterioles which regulate vascular resistance and tissue perfusion (e.g. the collateral side-branches above 300 μm², see Table 4). As a result, hind limb perfusion, determined by laser doppler or microspheres measurements, was increased more than three fold by PlGF treatment (Table 4). FIG. 6 is a laser doppler imaging showing high perfusion in the unaffected leg (B') as well as through the ligated (arrow) leg (A') seven days after femoral artery ligation and treatment with hPlGF-2, whereas in FIG. 5 a mouse which, after ligation, has been treated with a saline solution only shows low perfusion in the affected leg (A) compared to the unaffected leg (B). In contrast, a similar dose of $hVEGF_{165}$ was less efficient and consistent in inducing structural and perfusional changes. Thus, compared to VEGF, PlGF more efficiently enhanced growth of collateral side branches, which allows for a better functional recovery of the ischemic tissue, more particularly, the ischemic limb.

Example 6

Use of PlGF-VEGF Heterodimers

VEGF and PlGF have to bind as dimers to their cognate receptors. The activity of VEGF/VEGF-homodimers and PlGF/PlGF-homodimers is described above. However, VEGF and PlGF can also form heterodimers and have been documented in vivo (Cao, Y., Linden, P., Shima, D., Browne, F. & Folkman, J. In vivo angiogenic activity and hypoxia induction of heterodimers of placenta growth factor/vascular endothelial growth factor. J Clin Invest 98, 2507–11, 1996; DiSalvo, J. et al. Purification and characterization of a naturally occurring vascular endothelial growth factor placenta growth factor heterodimer. J Biol Chem 270, 7717–23, 1995). Their role in angiogenesis and arteriogenesis in vivo remains controversial, and no information is available whether VEGF/PlGF heterodimers can be used for therapeutic applications.

Using the same model of infarct revascularization as exemplified above, VEGF/PlGF heterodimer (from R&D, Abbingdon, UK) was administered via osmotic minipumps for a week at a dose of 10 microgram VEGF/PlGF heterodimer in wild type mice. The experimental data is reported in tables 6 and 7 as vessels/mm2 instead of as vessels/infarct. However the tables may be interpreted qualitatively in the same way as previous tables.

TABLE 5

| Growth factor | Endothelial-lined vessels (angiogenesis) | | |
|---|---|---|---|
| | Small vessels | Medium vessels | Large vessels |
| Control | 78 ± 2 | 25 ± 4 | 21 ± 3 |
| VEGF-PlGF heterodimer | 170 ± 25 | 51 ± 7 | 37 ± 4 |

TABLE 6

| Growth factor | Smooth-muscle-lined vessels (arteriogenesis) | | |
|---|---|---|---|
| | Small vessels | Medium vessels | Large vessels |
| Control | 25 ± 3 | 9 ± 1 | 5 ± 1 |
| VEGF-PlGF heterodimer | 38 ± 3 | 19 ± 2 | 9 ± 1 |

All values are statistically significant ($p<0.05$; treatment versus control)

As a summary, the present invention reports that PlGF stimulates the formation of mature and durable vessels in the ischemic heart, and enlarges collateral arterioles in the ischemic limb with marked perfusional and functional improvement. PlGF treatment achieves this therapeutic goal by unexpectedly combining two desirable properties, i.e. stimulating smooth muscle cells (SMC) simultaneously with endothelial cells (EC). PlGF thereby induces vessel growth in a more balanced manner than VEGF which preferentially stimulates EC. Importantly, the PlGF-induced mature vessels persisted for prolonged periods of more than one year, even long after the arteriogenic stimulus had disappeared, indicating that it may suffice to stimulate new vessels with a short-term delivery of PlGF. Moreover, PlGF shows the advantage of causing less side effects than VEGF in situations where chronic sustained delivery is required. In particular, PlGF did not cause the undesirable side effects of hyperpermeability, oedema and hemangioma formation associated with VEGF.

What is claimed is:

1. A method of treatment in a mammal after a skeletal muscle ischemic event, said method comprising administering to said mammal a therapeutically effective amount of placental growth factor (PlGF) wherein said PlGF results in functional improvement of a skeletal muscle in a mammal after said skeletal muscle ischemic event.

2. A method of treatment according to claim 1, wherein the said mammal is a human.

3. A method of treatment according to claim 1, wherein said skeletal muscle is selected from the group consisting of the musculature of head and neck, the musculature of thorax and abdomen, the musculature of back and the musculature of upper and lower limbs.

4. A method of treatment according to claim 1, wherein said functional improvement is a result of constructive angiogenesis, arteriogenesis and collateral vessel growth without the occurrence of hemodynamic side effects.

5. A method of treatment according to claim 3, wherein said functional improvement is evaluated by means of an endurance exercise test wherein the ischemic muscle under treatment is put under a stress condition.

6. The method of treatment according to claim 1, wherein said skeletal muscle ischemic event is a peripheral skeletal muscle ischemic event.

* * * * *

UNITED STATES PATENT AND TRADEMARK OFFICE
CERTIFICATE OF CORRECTION

PATENT NO.        : 7,105,168 B1                                Page 1 of 1
APPLICATION NO.   : 10/454242
DATED             : September 12, 2006
INVENTOR(S)       : Carmeliet et al.

It is certified that error appears in the above-identified patent and that said Letters Patent is hereby corrected as shown below:

On the Title Page

Item

[*] Notice:    Subject to any disclaimer, the term of this patent is extended or adjusted under 35 USC 154(b) by (49) days Delete the phrase "by 49" and insert -- by 110 days --

Signed and Sealed this

Nineteenth Day of February, 2008

JON W. DUDAS
*Director of the United States Patent and Trademark Office*